(12) United States Patent
Plonsky et al.

(10) Patent No.: US 10,369,718 B2
(45) Date of Patent: Aug. 6, 2019

(54) FLUSH CUT SAW

(71) Applicant: CANIS MAJOR TOOL COMPANY LLC, Sun Prairie, WI (US)

(72) Inventors: Richard D. Plonsky, Sun Prairie, WI (US); David Paul, Sun Prairie, WI (US)

(73) Assignee: CANIS MAJOR TOOL COMPANY LLC, Harshaw, WI (US)

( * ) Notice: Subject to any disclaimer, the term of this patent is extended or adjusted under 35 U.S.C. 154(b) by 486 days.

(21) Appl. No.: 14/828,163

(22) Filed: Aug. 17, 2015

(65) Prior Publication Data

US 2015/0352742 A1 Dec. 10, 2015

Related U.S. Application Data

(63) Continuation-in-part of application No. 11/300,854, filed on Dec. 15, 2005, now Pat. No. 9,108,334.

(60) Provisional application No. 60/636,301, filed on Dec. 15, 2004.

(51) Int. Cl.
| | |
|---|---|
| *B27B 5/08* | (2006.01) |
| *B23D 59/00* | (2006.01) |
| *A61B 17/14* | (2006.01) |
| *B27G 19/04* | (2006.01) |
| *B27B 9/04* | (2006.01) |
| *A61B 17/00* | (2006.01) |
| *A61B 90/00* | (2016.01) |

(52) U.S. Cl.
CPC .............. *B27B 5/08* (2013.01); *A61B 17/147* (2016.11); *B23D 59/006* (2013.01); *B27G 19/04* (2013.01); *A61B 2017/00017* (2013.01); *A61B 2017/00367* (2013.01); *A61B 2017/00561* (2013.01); *A61B 2090/0801* (2016.02); *B27B 9/04* (2013.01); *Y10T 83/04* (2015.04)

(58) Field of Classification Search
CPC .... B27B 5/08; B27B 5/29; B27B 5/30; B27B 5/32; B27B 9/04; B27B 9/00; B27B 9/02; A61B 17/147; A61B 2090/0801; A61B 2017/00017; A61B 2017/00367; A61B 2017/00561; B23D 59/006; B23D 45/16; B23D 1/00; B23D 1/08; B23D 1/18; B23D 1/20; B23D 3/00; B23D 3/02; B23D 9/00; B27G 19/04; Y10T 83/04
USPC ..................................................... 30/388–390
See application file for complete search history.

(56) References Cited

U.S. PATENT DOCUMENTS

| | | |
|---|---|---|
| 2,823,713 A | 2/1958 | Goldsmith |
| 3,583,106 A | 6/1971 | Dobbertin et al. |
| 4,262,420 A | 4/1981 | Nalley |
| 4,809,438 A | 3/1989 | Nagashima et al. |
| 4,847,721 A | 7/1989 | Notholer et al. |
| 4,858,662 A | 8/1989 | Bosten et al. |

(Continued)

OTHER PUBLICATIONS

Crain No. 820 Heavy-Duty Undercut Saw, http://www.craintools.com/pages/more_pages/820_more.html.

(Continued)

*Primary Examiner* — Phong H Nguyen
(74) *Attorney, Agent, or Firm* — Casimir Jones, S.C.; Tyler J. Sisk

(57) ABSTRACT

This invention relates generally to power tools, and more particularly to a portable, multifunction saw and uses thereof (e.g., for household, commercial (e.g., for use in window removal and replacement) and medical (e.g. for bone cutting) applications).

13 Claims, 16 Drawing Sheets

(56) References Cited

U.S. PATENT DOCUMENTS

| | | | |
|---|---|---|---|
| 4,913,204 A | 4/1990 | Moores et al. | |
| 5,013,195 A | 5/1991 | Strazar | |
| 5,263,283 A | 11/1993 | Rudolf et al. | |
| 5,441,450 A | 8/1995 | Fein et al. | |
| 5,657,804 A | 8/1997 | Lee | |
| 5,674,119 A | 10/1997 | DesRosiers | |
| 5,694,992 A | 12/1997 | Kikuchi | |
| 5,815,932 A | 10/1998 | Presher et al. | |
| 5,967,013 A | 10/1999 | McKenzie et al. | |
| 5,974,674 A | 11/1999 | Kelly | |
| 5,988,240 A | 11/1999 | Markus | |
| D423,898 S | 5/2000 | Kelley | |
| 6,336,483 B1 * | 1/2002 | Smith | B27F 5/02 144/136.95 |
| 6,402,415 B1 | 6/2002 | Eberle, III | |
| 6,569,001 B2 | 5/2003 | Ruldolf et al. | |
| 2003/0140507 A1 * | 7/2003 | Lagaly | B23D 49/162 30/392 |

OTHER PUBLICATIONS

Fein WSG 12-150, htto://www.feinus.comp/p/NEWgrinder/newwsg.html.

* cited by examiner

FLUSH CUT SAW

This application is a continuation-in-part of U.S. patent application Ser. No. 11/300,854, filed Dec. 15, 2005, which claims the benefit of U.S. Provisional Application No. 60/636,301 filed Dec. 15, 2004, the disclosure of each of which is incorporated herein by reference in their entireties.

FIELD OF THE INVENTION

This invention relates generally to power tools, and more particularly to a portable, multifunction saw assembly comprising a protective guard-guide subassembly (e.g., for household, commercial (e.g., for use in general carpentry and finish carpentry) and medical (e.g. for bone cutting) applications).

BACKGROUND OF THE INVENTION

Saws are used for a variety of purposes. For example, saws are used in a variety of carpentry-type applications. For example, when a window begins to fail (e.g., warp, rot or leak) the costs in terms of energy costs add up. Window replacement serves as a means to overcome the expenses associated with failing old windows. New window technology has resulted in dramatic savings and increased comfort for home-owners through the use of reformulated frame materials and glazing products that require significantly less maintenance. However, current methods and devices used for the removal of old windows are time consuming, damaging and often dangerous. For example, current methods (e.g., use of a chisel and hammer or a reciprocating saw) lead to disruption of the inside trim and destruction of wood that otherwise need not be replaced.

Saws also find use in medicine (e.g., orthopedic medicine). For example, knee replacement surgery typically involves removal of all or a portion of the existing knee joint, and the insertion of artificial prostheses (or components). The orthopedic surgeon utilizes a series of sequential instruments and guides to cut and shape the patient's host bone on which implants are fixed, resulting in replacement of the worn surfaces of all three compartments of the knee with smooth articulating artificial surfaces.

Currently available saws are not ideal for many tasks (e.g., window removal or use in the operating room) because of safety concerns. Specifically, some saws lack protective guards that cover the entire blade of the saw while others may have a partially enclosing protective cover that requires manual adjustment by the user. Both of these types of guards prohibit a user from getting close enough to a cut site to permit the blade to make a flush cut. Still other saws do not permit the user to make a straight cut. Therefore, a need exists for a safer and easier to use saw (e.g., that allows for safer, more efficient and less expensive removal and replacement of old windows, or, that permits a straight cut to be made in a safe manner (e.g., for use in commercial or medical settings).

SUMMARY OF THE INVENTION

This invention addresses the problems outlined above by providing a portable, multifunction saw assembly comprising a protective guard-guide subassembly (e.g., for household, commercial (e.g., for use in general carpentry and finish carpentry) and medical (e.g. for bone cutting) applications).

Accordingly, in some embodiments, the present invention provides a saw assembly, comprising: an electric motor subassembly, the electric motor subassembly having an electric motor adapted to produce rotational movement about a first axis of rotation and a spindle rotatably powered by the electric motor for rotation about a second axis of rotation that is perpendicular to the first axis of rotation; a blade mounted on the spindle, and a retractable, fully enclosing blade guard-guide subassembly, the blade guard-guide subassembly comprising a top main guard-guide slidably mounted on the electric motor subassembly and a bottom guard-guide plate fixed to the top main guard-guide assembly. In some embodiments, the blade is mounted on a flush-mount comprising a countersunk dimple with a hardened screw. In some embodiments, the blade is mounted on a blade spacer/adapter removably attached to the saw. In some embodiments, the blade is mounted onto the spacer/adapter using three or more counter sunk screws. The present invention is not limited by the type of material used to make the spacer. Indeed, a variety of materials are contemplated to be useful for making a spacer of the present invention including, but not limited to, TEFLON, aluminum, DELRIN, copper, rubber or plastic. In some embodiments, the blade has teeth that extend to an outer circumference of the blade. In some embodiments, the blade guard-guide subassembly is spring-loaded. In some embodiments, the blade guard-guide subassembly fully encloses the blade until the blade guard-guide subassembly operably contacts a surface. In some embodiments, the operable contact comprises physical contact between a surface and the guard-guide subassembly such that the blade guard-guide moves into a retracted position, wherein the amount of retraction directly correlates with the amount of pressure asserted against the guard-guide subassembly by the surface. In some preferred embodiments, a saw of the present invention is used to make a flush-cut. For example, in some embodiments, the blade comprises oblong cutouts for attachment (e.g., with screws) to a flanged hub. In some embodiments, the flanged hub attaches to and drives the blade. The present invention is not limited by the configuration of the flanged hub. Indeed, a variety of configurations are possible including, but not limited to, a flanged hub with an oval section that protrudes from the hub a dimension equal to the thickness of the blade (e.g., so as to be flush with the blade when the two are joined by screws (e.g., machine screws). In some embodiments, the blade is attached to a spacer/adapter. The spacer/adapter may be made of any suitable material. The present invention is not limited by the type of material used to make the spacer. Indeed a variety of materials are contemplated to be useful including, but not limited to, TEFLON, copper, DELRIN, aluminum, rubber or plastic. Furthermore, the spacer/adapter may comprise one or more (e.g., three or more) holes for receiving screws for attachment of the blade. In some embodiments, the blade alternatively provides other means for attaching to the saw (e.g., at three or more locations to provide a stable attachment). In some embodiments, the blade and/or guard-guide subassembly comprises a spacer so as to minimize run out or galloping of the blade on a surface to be cut (e.g., thereby preventing uneven blade exposure to a surface during cutting).

The present invention is not limited by the type of surface contacted. Indeed, many types of surfaces are contemplated to be contacted by the saw including wood, plastic, metal, glass, ceramic, tile and bone. In some embodiments, the maximal amount of retraction of the guard-guide subassembly exposes 10% of the blade (in some embodiments, the maximal amount of retraction exposes 10-25% of the blade, in some embodiments, the maximal amount of retraction exposes 25-50% of the blade, in some embodiments, the maximal amount of retraction exposes 50-75% of the blade, and in still other embodiments, the maximal amount of retraction exposes greater than 75% of the blade). In some embodiments, the cutting blade is adjustably positioned with an adjustable stop for depth in vertical alignment with the cutting surface. In some embodiments, the blade guard-guide subassembly comprises an aluminum alloy or plastic. In some embodiments, the bottom guard-guide plate is fixed to the top main guard-guide (e.g., via screws). In some embodiments, the bottom guard-guide plate is fixed to the top main guard-guide (e.g., via screws). In further embodiments, the guard-guide subassembly comprises a retractable (e.g., spring loaded) bottom guard-guide that is retracted (e.g., fully to completely expose the bottom portion of the blade (e.g., for flush-cutting)) separate from retraction of the top, main guard-guide (e.g., the top, main guard guide will remain in place while a user retracts the bottom guard (e.g., to make a flush-cut). In some embodiments, the fully enclosed (fixed bottom guard) guard-guide assembly incorporates a "U" shaped notch so as to allow a pipe or other object whose diameter or width is less than the notch, to become engulfed in the notch as the cut proceeds.

In some embodiments, the guard-guide subassembly comprises angled housing. In some embodiments, the saw assembly further comprises an electric motor with a momentary contact switch (e.g., a dead man's switch). In some embodiments, the contact switch comprises a variable speed throttling switch. In some embodiments, the throttling switch permits the blade speed to ramp up or down. In some embodiments, the saw assembly further comprises a handle. In some embodiments, the electric motor is adapted to operate at rotational speeds between 3000-5000 revolutions per minute (rpm) (in some embodiments, the motor operates at speeds between 5000-7000 rpm, in other embodiments, the motor operates at speeds between 7000-10,000 rpm, and in still other embodiments, the motor is adapted to operate at rotational speeds greater than 10,000 rpm). In some embodiments, the blade comprises a carbide tip. In some embodiments, the outer diameter of the blade is between 2-4 inches (in some embodiments, the diameter is between 4-5 inches, in still other embodiments, the blade diameter is between 5-7 inches, and in some embodiments, the diameter of the blade is greater than 7 inches. In some embodiments, the saw assembly further comprises a vacuum attachment.

The present invention also provides a method of cutting a surface using the saw of the present invention. The present invention is not limited by the nature of the surface being cut. Indeed, a variety of surfaces are contemplated, including, but not limited to, wood, plastic, metal, glass, ceramic, cement, tile and bone. In some embodiments, the guard-guide of the saw permits a user to make a straight cut in a surface (e.g., house siding (e.g., wood cement, composite or the like). In some embodiments, cutting a surface comprises making a flush, plunge cut in the surface. In some embodiments, cutting a surface comprises undercutting a door jamb. In some embodiments, cutting a surface comprises undercutting a base molding.

The present invention also provides a method of removing windows comprising using saws of the present invention and related devices.

The present invention further provides a method of removing a window, comprising removing an existing sash of the window, the removing comprising cutting stops present in the window, the cutting comprising using a saw configured so as not to have a blade exposed to the user during any portion of its use, wherein the method does not disrupt the inside window trim. In some embodiments, the window is replaced with a new window after the old window is replaced. In some embodiments, there is no need for new pieces of wood to assist in the replacement of the old window (e.g., in some embodiments, only caulk is needed).

A sash is the framework into which glass is set. Double-hung windows have two sashes: an upper and a lower sash. The window sashes slide within a window frame. The top horizontal member of the frame is called the head. The side frames are called jambs. Concealed behind the side jambs on old double-hung windows may be heavy metal sash weights connected to the sash with rope-and-pulley systems. The weights provide a counterbalance that makes the sash easier to open. Newer windows use a revolving drum in the head or tubed tension springs in the side jambs instead of sash weights. The lower horizontal part of the window frame is called the sill. A series of stops attached to the jambs provides channels in which the sashes can slide. Blind stops are permanently attached to the outside edges of the jambs, but both a parting stop (separating the two sashes) and an inside stop can be pried loose (or cut) to remove a sash. Interior casings at the sides and top and an apron across the bottom cover any gaps between the window frame and the walls. The lower sash comes to rest behind a flat stool or interior sill; its outside counterpart, the exterior sill, is sloped so that water will run off.

In some embodiments, the present invention provides a saw assembly comprising a motor; a linkage for converting rotating power of the motor into linear reciprocating (e.g., vibrating) movement; a slider shaft mounted at an end of the linkage having an angle of approximately 90 degrees with respect to the linkage; a slider, for attaching a saw blade, which moves reciprocatingly along the slider shaft, and a fully enclosing blade guard-guide subassembly, the blade guard-guide subassembly comprising a top main guard-guide slidably mounted on the electric motor subassembly and a bottom guard-guide plate fixed to the top main guard-guide assembly. In some embodiments, the blade used with reciprocating, vibrating or oscillating saw is non-circular (e.g., is a file saw blade).

DESCRIPTION OF PREFERRED EMBODIMENTS

Figure 1:
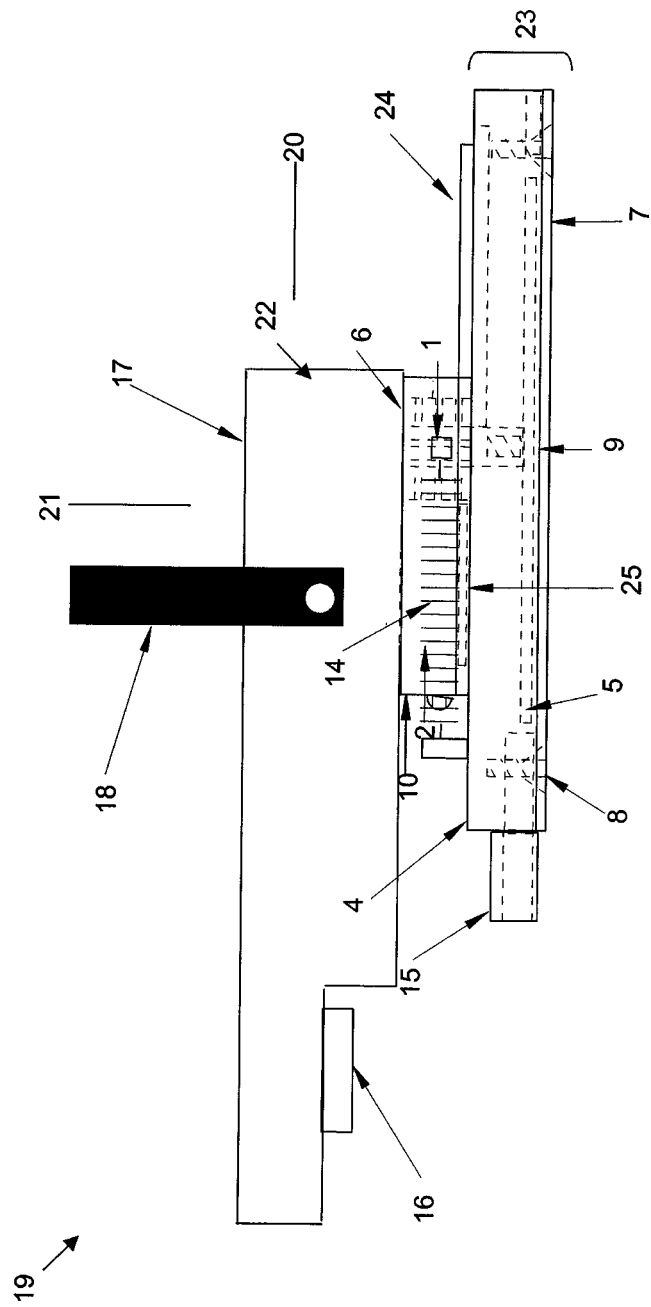
FIG. 1 depicts a side view of a saw assembly constructed according to the invention.
Figure 2:
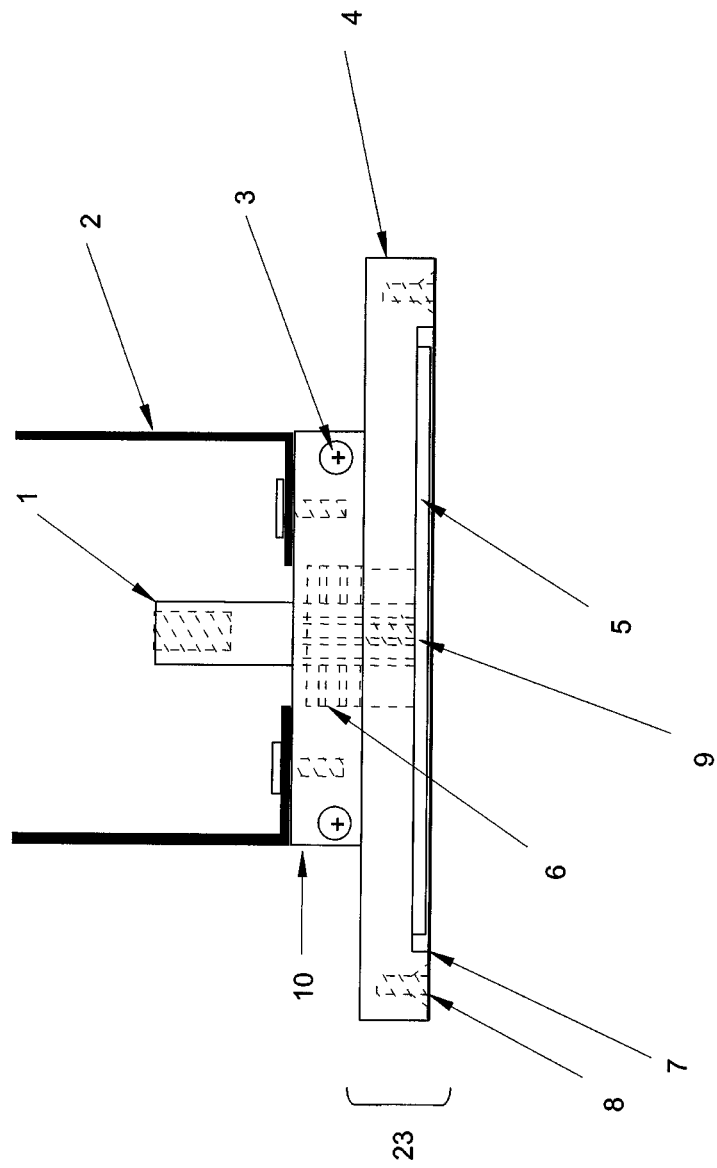
FIG. 2 depicts a frontal view of a saw assembly constructed according to the invention.
Figure 3:
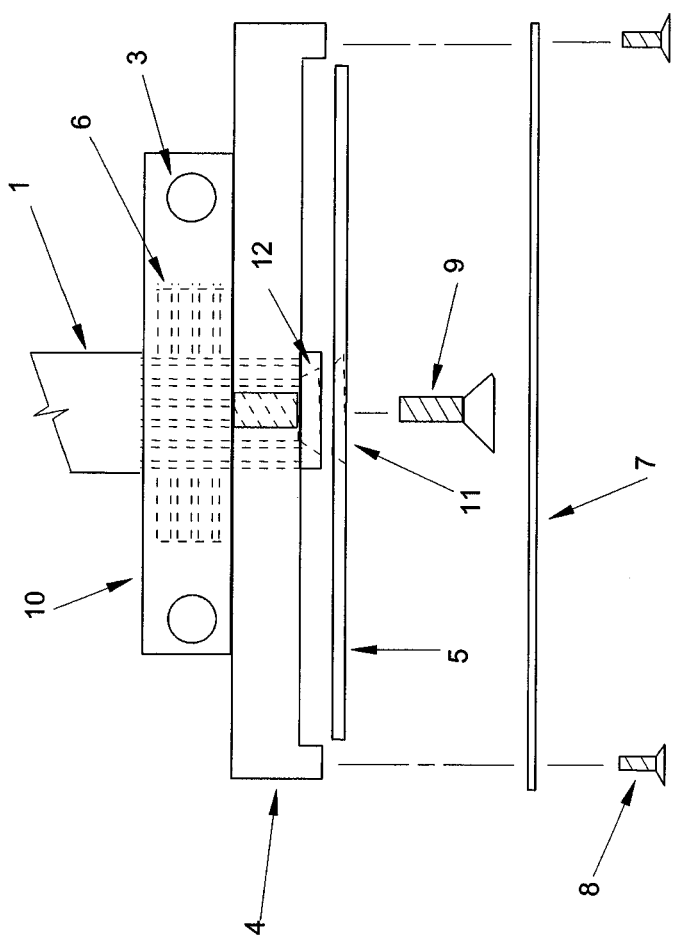
FIG. 3 depicts an exploded frontal view of a saw assembly constructed according to the invention.
Figure 4:
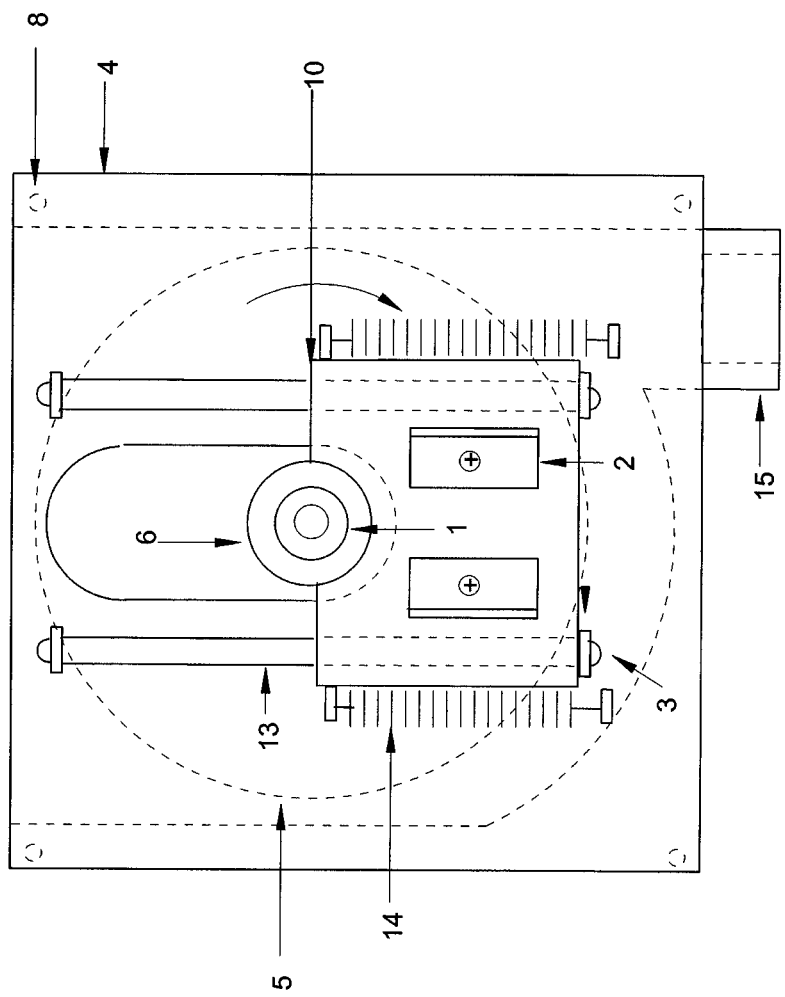
FIG. 4 depicts a top view of a saw assembly constructed according to the invention.

Described below are certain preferred embodiments. Although the invention has been described in connection with specific preferred embodiments, it should be understood that the invention as claimed should not be unduly limited to such specific embodiments. Indeed, various modifications of the described compositions and methods of the invention that are obvious to those skilled in the field are intended to be within the scope of the claimed invention.

FIGS. 1-4 of the drawings show various details of one embodiment of a saw assembly 19 (FIG. 1) constructed according to the invention. Generally, the saw assembly 19 includes an electric motor subassembly 17 (FIG. 1) and a spindle 1 (FIGS. 1-4, and 6) rotatably powered by the electric motor 17. These components can take any of various forms. For example, in some embodiments, the electric motor subassembly 17 is of the 4-inch, right angle drive grinder model 8313 that is commercially available under the trademark TALON from Jenn Feng U.S.A. of Lincolnshire, Ill. That electric motor assembly weighs about five pounds and measures roughly 2½ inches in outside diameter and about ten inches long so that it can be conveniently grasped with one hand. In some embodiments, the electric motor subassembly is a 4½ inch to 6 inch, right angle drive grinder (e.g., model numbers WSS6.5-115, WSS 12-125, WSG 12-125, WSG 12-70 E. WSG 12-150) available under the trademark FEIN Angle Grinders from C. & E. FEIN, Stuttgart, Germany.

In the illustrated embodiment, the electric motor subassembly 17 is a high speed motor operating on 120-volt, 60 Hz, 650-1200-watts of power at between 3000-5000 revolutions per minute (rpm) (in some embodiments, the motor operates at speeds between 5000-7000 rpm, in other embodiments, the motor operates at speeds between 7000-10,000 rpm, and in still other embodiments, the motor is adapted to operate at rotational speeds greater than 10,000—e.g., a no load speed of 12,000). The electric motor subassembly 17 is adapted to produce a rotational movement about a first axis of rotation 20 (FIG. 1) and the spindle 1 is rotatably powered by the electric motor subassembly 17 for rotation about a second axis of rotation 21 (FIG. 1) that is perpendicular to the first axis of rotation 20. For that purpose, the electric motor subassembly 17 includes a right angle drive 22 that couples rotational movement by suitable known means from the electric motor subassembly 17 to the spindle 1.

Figure 12:
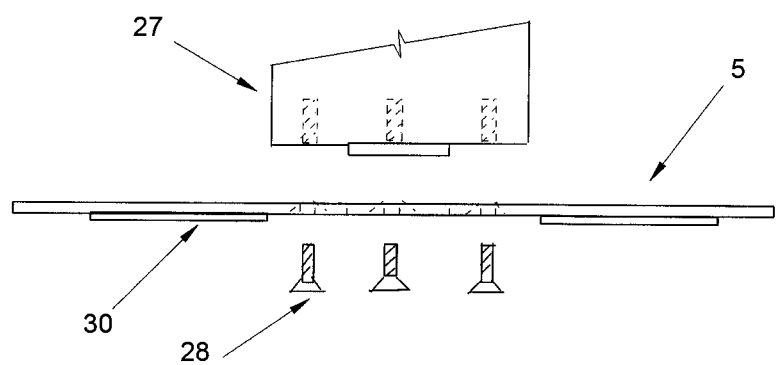
FIG. 12 shows a side view of one embodiment of a spacer for use with a blade of the present invention.

In some embodiments, a circular blade 5 (FIGS. 1-4, and 6) is removably mounted on the spindle 1 with a countersunk blade attachment screw 9 (FIGS. 2 and 3) that screws into a countersunk spindle hole 12 (FIG. 3) on the spindle 1. Having the blade mounted on a flush-mount (e.g., comprising a countersunk dimple with a hardened screw) allows the blade to make a flush cut. In some embodiments, the blade 5 comprises oblong cutouts for attachment (e.g., with screws 9) to a flanged hub 27 (See FIGS. 7, 8, 11, and 12). In some embodiments, the flanged hub 27 attaches to and drives the blade 5. The present invention is not limited by the configuration of the flanged hub 27. Indeed, a variety of configurations are possible including, but not limited to, a flanged hub 27 with an oval section that protrudes from the hub a dimension equal to the thickness of the blade 5 (e.g., so as to be flush with the blade when the two are joined by screws 28 (e.g., machine screws). In some embodiments, the blade 5 is attached to a spacer/adapter 30 (See FIG. 12). The spacer/adapter 30 may be made of any suitable material. The present invention is not limited by the type of material used to make the spacer. Indeed a variety of materials are contemplated to be useful including, but not limited to, TEFLON, copper, DELRIN, aluminum, rubber or plastic. Furthermore, the spacer/adapter 30 may comprise one or more (e.g., in preferred embodiments, the spacer comprises three) holes for receiving screws 28 for attachment of the blade 5. Thus, in preferred embodiments, the blade 5 and/or guard-guide subassembly comprises a spacer 30 so as to minimize run out or galloping of the blade on a surface 26 to be cut (e.g., leading to uneven blade exposure to a surface during cutting).

In a preferred embodiment, the blade 5 is not only removable, but also reusable, disposable and/or easily replaced with a blade 5 possessing a desired characteristic(s) (e.g., a carbide tipped blade, a grinder wheel, or a file). The present invention is not limited by the nature of the blade 5. The blade 5 may comprise one or more materials. The material may be selected from, but not limited to, carbide tipped blades, diamond tip blades, a grinder wheel or a sanding wheel. In some embodiments, the blade 5 is a sterile blade 5 (e.g., for use in medical procedures). In some embodiments, the blade 5 comprises one or more materials useful for medical procedures (e.g., including, but not limited to, a medically useful coating). In some embodiments, the blade 5 has teeth that extend to an outer circumference of the circular blade 5. In some embodiments, the blade has a chamfered shoulder 29 (See, e.g., FIG. 11). A saw assembly 19 that utilizes a blade 5 comprised of one or more of these materials can be used for cutting many types of surfaces 26 (FIG. 6), including, but not limited to, wood, plastic, metal, glass, cement, ceramic, cement, tile or bone. The invention is not limited by a particular size blade 5. In some embodiments, the blade 5 is a 4-inch diameter blade. In some embodiments, the blade 5 chosen has a diameter from 2 inches to 4 (in some embodiments, the diameter is between 4-5 inches, in still other embodiments, the blade diameter is between 5-7 inches, and in some embodiments, the diameter of the circular blade is greater than 7 inches or less than 2 inches (e.g., is 0.5-2 inches in diameter).

In some embodiments, a blade guard-guide subassembly 23 (FIG. 2) is mounted to guide rods 13 (FIGS. 4 and 6) attached to a sliding bearing block 10 (FIGS. 1, 4, 6 and 9) comprising return springs 14 (FIGS. 4, 6 and 10) or other material that spring biases the guard-guide subassembly 23 toward the closed position depicted in FIGS. 1-4. In some embodiments, the guard-guide subassembly is adjustably controlled with an adjustable stop (e.g., for adjustably positioning the depth of the cutting blade (e.g., the length of the blade exposed beyond the guard-guide subassembly (e.g., determining the cutting depth))).

Figure 6:
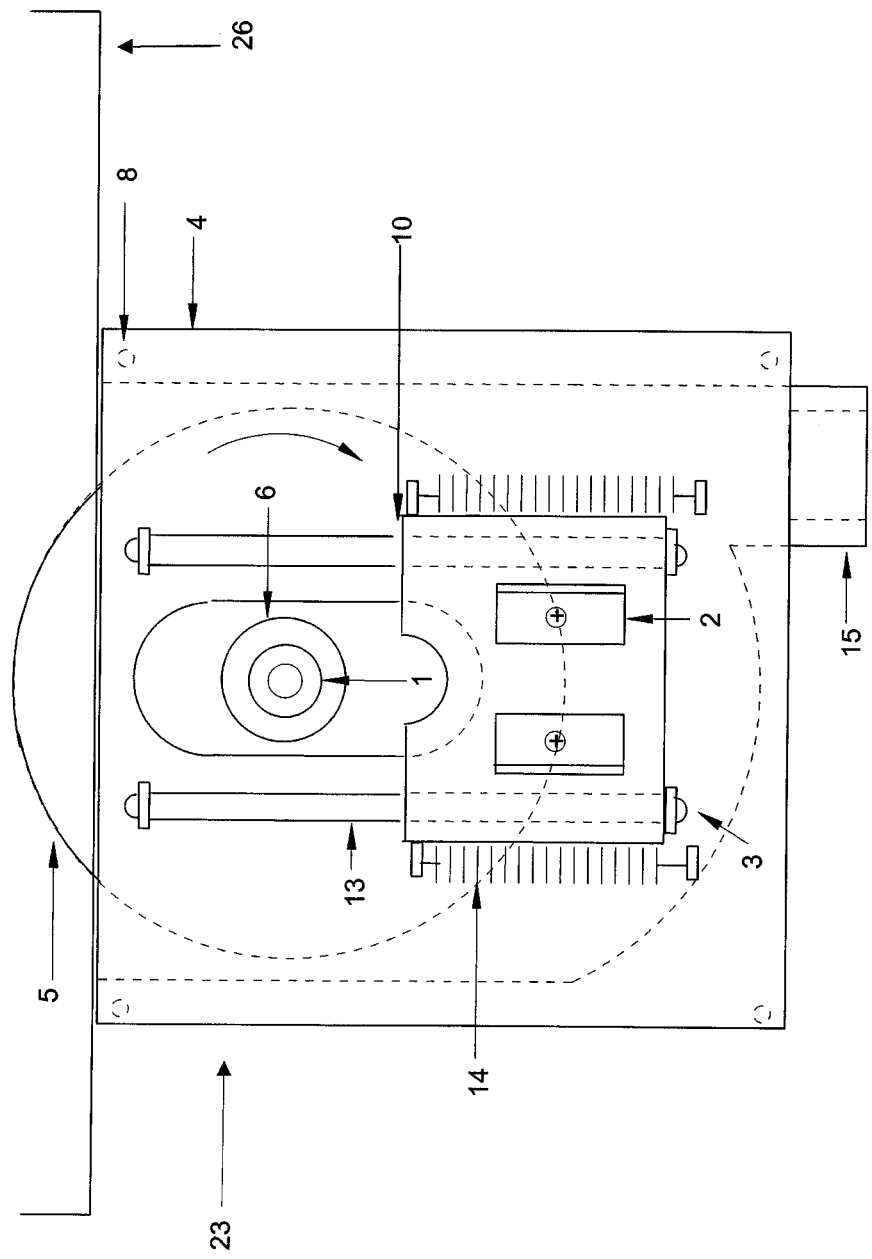
FIG. 6 depicts a top view of a saw assembly constructed according to the invention with the blade partially deployed into a surface.
Figure 7:
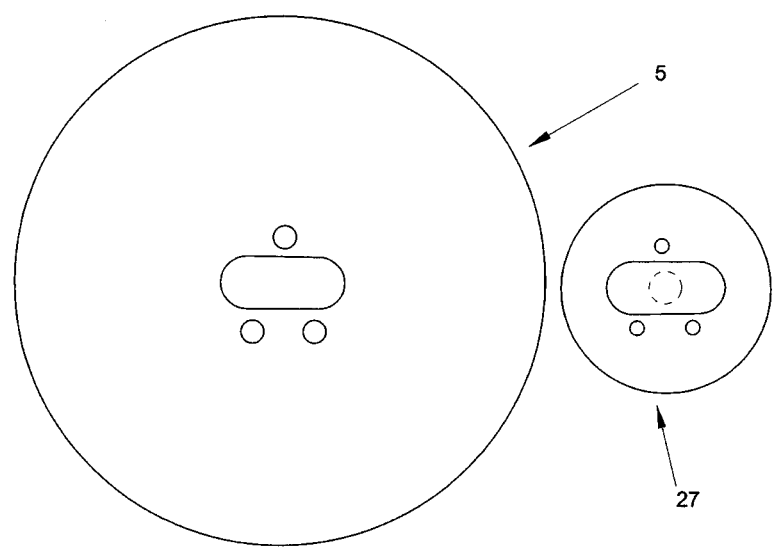
FIG. 7 shows a top view of one embodiment of a blade and blade spacer of the present invention.
Figure 8:
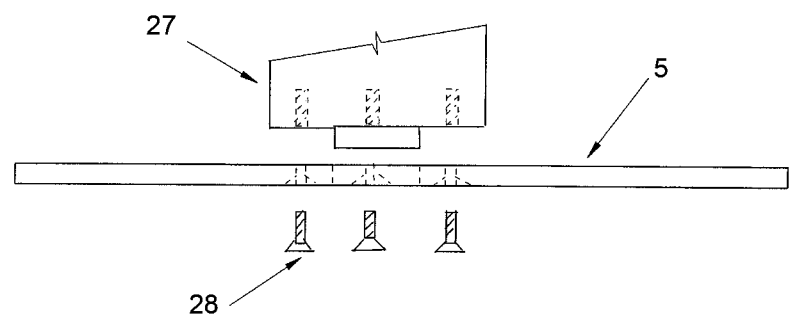
FIG. 8 shows a side view of one embodiment of a blade and blade spacer of the present invention.
Figure 9:
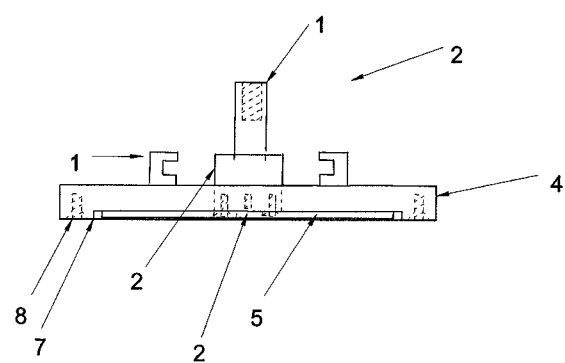
FIG. 9 shows one embodiment of a guard-guide subassembly with screws used to attach a blade spacer to a blade.

In some embodiments, a sliding bearing block 10 is mounted on the electric motor subassembly 17 via an attachment bracket 2 (FIGS. 1 and 6). In an alternative embodiment, a sliding lug 25 (FIG. 1) is attached to a bearing block 10 mounted on the electric motor subassembly 17. In some embodiments, a slide channel 24 (FIG. 1), connected to the lug 25, holds the guard-guide subassembly 23 in place over the blade. In one preferred embodiment, the guard-guide subassembly 23 covers the entire blade 5 when not in operable contact with a surface.

The guard-guide subassembly 23 comprises a top, main guard-guide 4 (FIGS. 1-4, 6, 9 and 10) and a bottom guard-guide 7 (FIGS. 1-3, and 9). The present invention is not limited by the nature of the material that comprises the guard-guide subassembly 23. Indeed, a variety of materials are contemplated including, but not limited to, aluminum, aluminum alloys, plastic, plastic compounds, metal, or metal alloys. The guard-guide subassembly 23 is configured such that there is clearance between itself and the blade 5. In some embodiments, the guard guide subassembly 23 further comprises ports 15 (FIGS. 1, 4, 6, 10 and 17) for attachment of additional components (e.g., a sawdust collecting bag (e.g., attached to a vacuum source). In some embodiments, the guard-guide subassembly 23 (e.g., comprising the top, main guard guide 4) is angled (See, e.g., FIG. 10). It is contemplated that use of an angled guard guide subassembly may permit cuts (e.g., flush cut of a door jamb, baseboard, or base molding) that are not possible with a non-angled guard-guide.

According to one aspect of the invention, the blade guard-guide subassembly 23 retracts when in operable contact with a surface 26. In some embodiments, operable contact comprises a physical contact between a surface 26 and the guard-guide subassembly 23, with the amount of retraction directly corresponding to the amount of pressure asserted against the guard-guide subassembly 23 by the surface 26. In a preferred embodiment, the blade 5 is not exposed above the surface 26 of which it is cutting (i.e., the guard-guide subassembly 23 continues to enclose that part of the blade 5 that does not penetrate the surface 26; See, e.g., FIGS. 6 and 10, wherein the blade 5 remaining protected by the guard-guide subassembly 23 is depicted by hashed lines and that portion of the blade 5 below the surface 26 to be cut is depicted by a solid line). In some embodiments, the electric motor subassembly 17 cannot run without contact between the guard-guide subassembly 23 and a surface 26 to be cut. In still further embodiments, the guard-guide subassembly 23 comprises a retractable (e.g., spring loaded) bottom guard-guide 7 that can be retracted fully (e.g., to completely expose the bottom portion of the blade (e.g., for flush-cutting)) separate from retraction of the top, main guard-guide 4 (e.g., the top, main guard guide will remain in place while a user retracts the bottom guard 7 (e.g., to make a flush-cut) and will not retract until in operable contact with a surface 26). The invention is not limited by the means by which the bottom guard-guide is made retractable. Indeed, any means known in the art that permits the bottom guard-guide to be retracted separately from the top, main guard-guide can be used. For example, in some embodiments, the bottom guard-guide exists as a discrete component separate from the top main guard-guide (e.g., can be independently removed and reinstalled by an operator. In some embodiments, the bottom guard-guide is retractable (e.g., partially or fully (e.g., via a spring loaded mechanism)) from the top main guard guide that itself is not spring loaded (e.g., it is fixed to the saw). In some embodiments, the bottom guard-guide is retracted (e.g., partially or fully) separate from retraction of the top main guard-guide using a eccentric cam (e.g., in order to reduce retraction tension (e.g., at full retraction of the bottom guard-guide)). In some embodiments, the bottom guard-guide is retracted (e.g., partially or fully) separate from retraction of the top main guard-guide using a spiral torsion spring. In some embodiments, the bottom guard-guide is retracted (e.g., partially or fully) separate from retraction of the top main guard-guide utilizing differential spring tensions (e.g., bottom guard-guide spring requires less force to extend or load than top guard-guide spring, thereby allowing bottom guard-guide to retract while the top guard-guide remains in place (e.g., until such time that the guard-guide subassembly makes physical contact with a surface and the amount of retraction directly corresponds to the amount of pressure asserted against the guard-guide subassembly by the surface to be cut)).

In one embodiment, the bottom guard-guide is retracted separately from the top, main guard-guide via making the bottom guard-guide spring loaded with an eccentric cam (e.g., thereby reducing retraction tension at full retraction of the bottom-guard-guide). In some embodiments, the saw is configured such that an operator must have two hands upon the saw in order for the saw to run (e.g., when the bottom guard-guide 7 is completely retracted prior to use of saw).

The invention is not limited by the type of material cut by a saw of the invention. Indeed, any type of material may be cut including, but not limited to, wood, stone, brick, bone, plastic, composite, metal, or other material. In some embodiments, a saw incorporates a motor subassembly and a guard-guide subassembly that allows the operator to produce a flush cut. For example, a saw of the invention allows an operator of the saw to remove or move away (e.g., slide or retract) the bottom guard portion of the guard-guide subassembly (e.g., thereby permitting the bottom of the blade/abrasive cutter to contact a surface parallel to the bottom surface of the blade/abrasive cutter. In one embodiment, a blade or abrasive cutter of the saw assembly is deployed forward parallel to the surface (e.g. in order to cut or abrade a material proud of that surface).

In some embodiments, the saw assembly comprises one or more safety features that protect an operator and/or bystander from the blade/abrasive cutter. In some embodiments, the saw assembly comprises one or more safety features that protect an operator and/or bystander from dust and/or debris. Safety feature include, but are not limited to, a guard-guide that fully, or partially, depending on the configuration, covers the blade/abrasive cutter. In some embodiments, a saw assembly comprises a spring-loaded guard-guide (e.g., that retract during operation) that extends to cover the blade/abrasive cutter when the operator releases pressure, or the saw slips from the operator's hand or hands. In some embodiments, a saw assembly comprises a momentary contact switch (also known as a "dead man's" switch) that removes power from the motor if deliberately released by the operator, or released inadvertently, such as if the saw were to slip from the operator's hand or hands. In some embodiments, a saw assembly comprises a throttling momentary contact switch that provides "dead man" protection as well as variable speed capability to allow the operator to vary the speed of the blade/abrasive cutter in direct proportion to pressure applied to the switch by the operator. In some embodiments, a saw assembly comprises a mechanical lock (e.g., a spring-loaded pin, a hook loaded by a tension spring or other mechanical device) that acts as a "safety" and prevents the momentary contact "dead man" switch from being depressed (e.g., completing an electrical circuit without deliberate and independent action by the operator to disengage it prior to depressing the switch). In some embodiments, a saw assembly comprises a guard-guide that ports away dust and/or debris generated during operation. For example, in some embodiments, a saw assembly comprises a guard-guide that vents dust and debris generated during operation into a port diverting it away from the operator (e.g., into a vacuum or other retention device). In some embodiments, a saw assembly comprises an electric sensing circuit (e.g., via electromechanical switches, or electronic sensors) that prevents the motor from operating (e.g., from starting to run or continuing to run) without both the operator's hands placed on a specific portion of the saw assembly (e.g., specific handles). For example, in one embodiment, if an operator removes one or both hands from the saw (e.g., where electromechanical sensors are located (e.g., within handles)), power is removed from the motor of the saw assembly and the saw will not operate.

Figure 13:
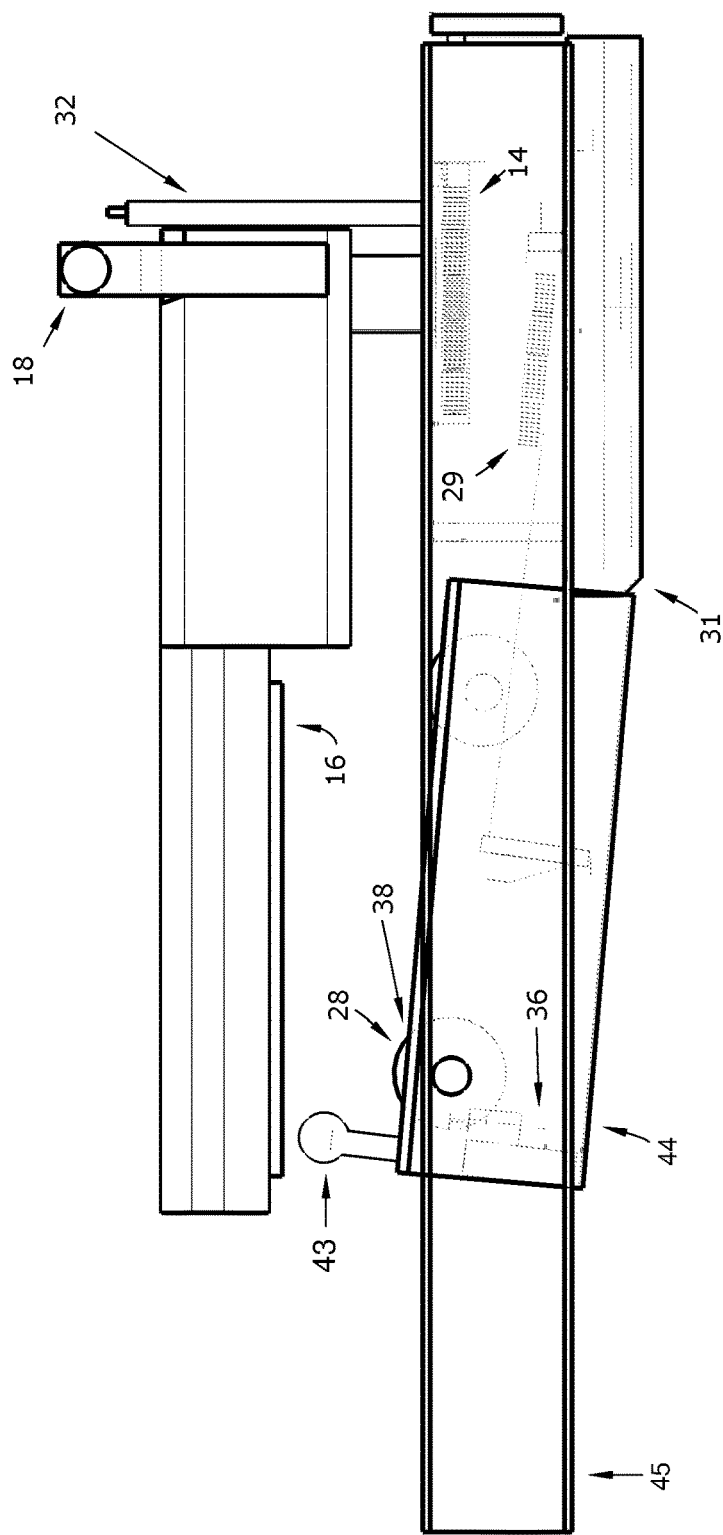
FIG. 13 depicts a side view of one embodiment of a saw assembly comprising a guard-guide subassembly comprising a retractable bottom guard-guide that is retracted separate from retraction of the top, main guard-guide.
Figure 14:
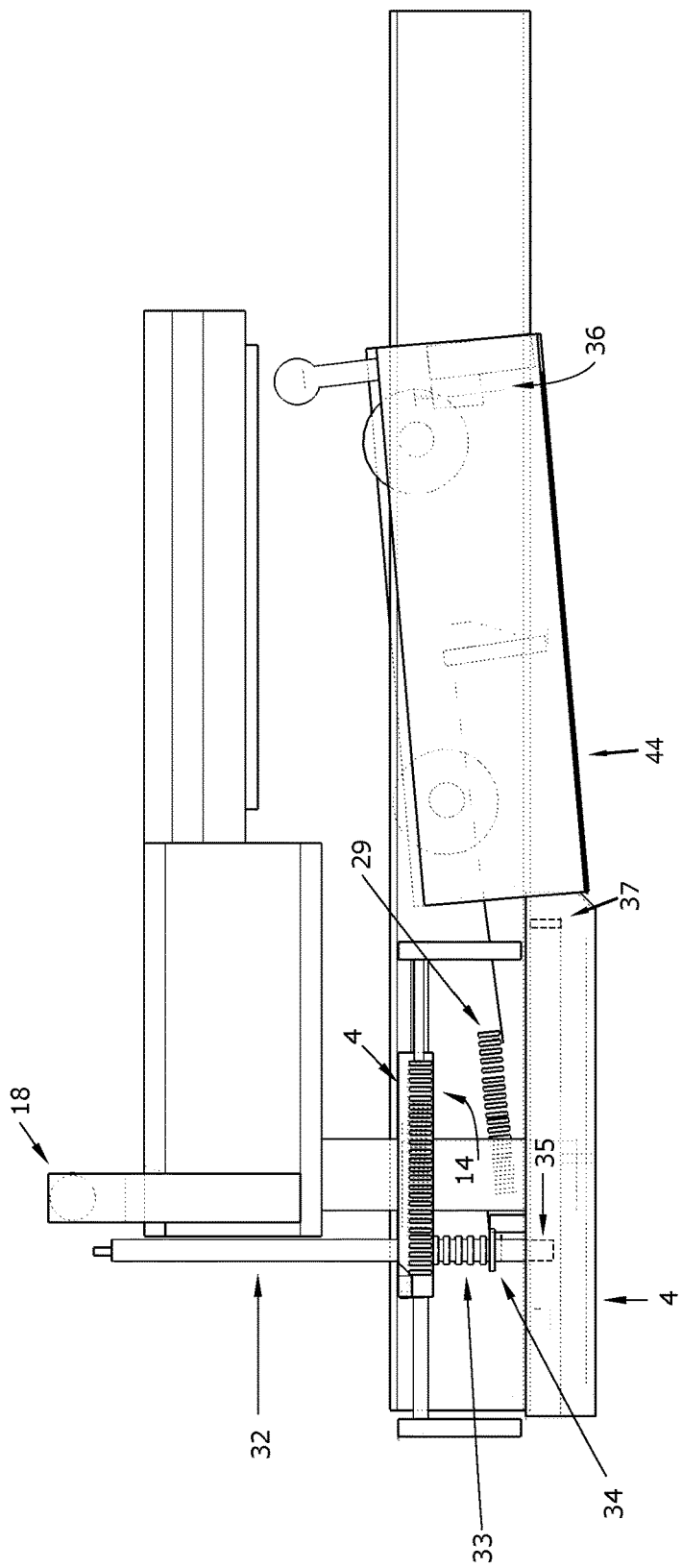
FIG. 14 depicts a cutaway side view of one embodiment of a saw assembly comprising a guard-guide subassembly comprising a retractable bottom guard-guide that is retracted separate from retraction of the top, main guard-guide.
Figure 15:
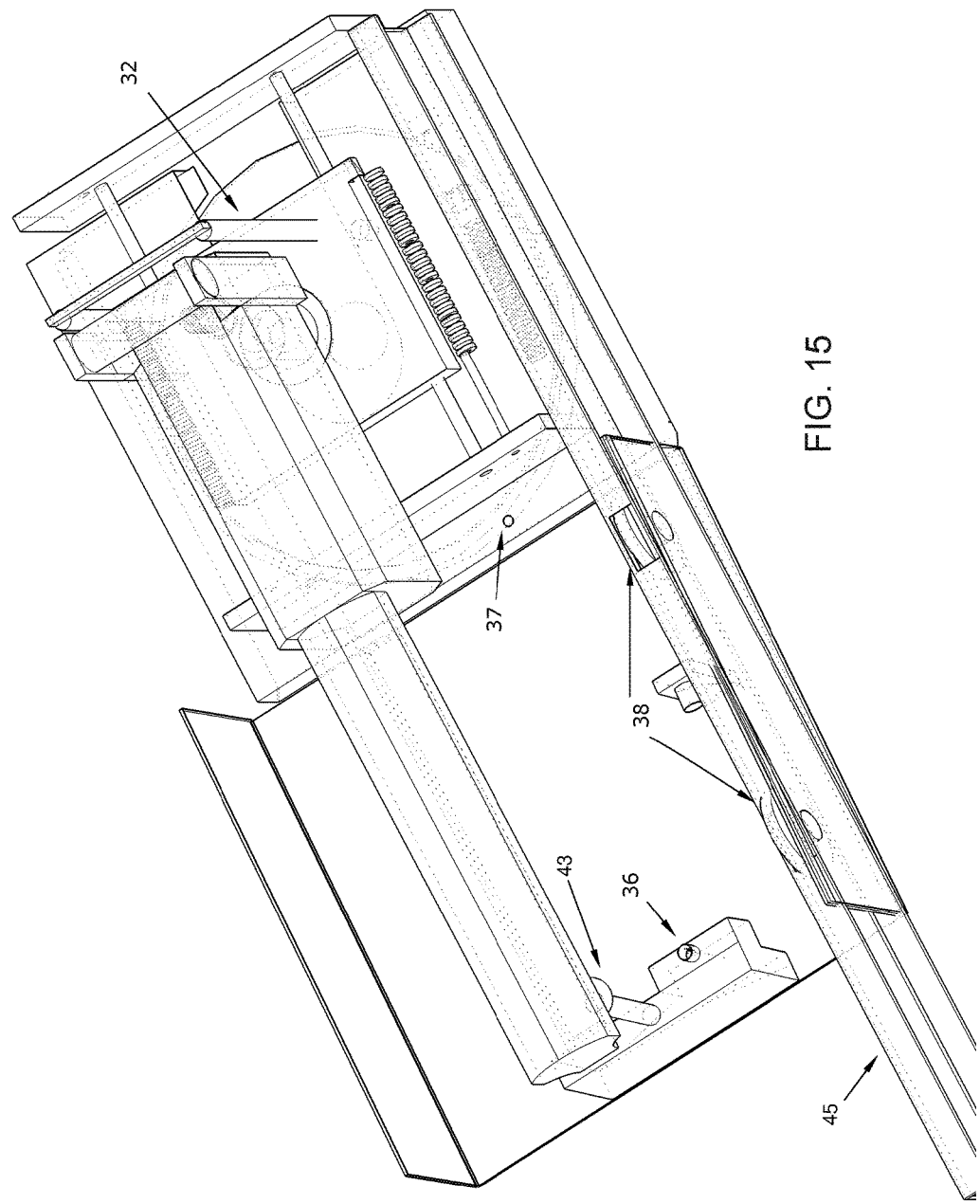
FIG. 15 depicts an oblique top view of one embodiment of a saw assembly comprising a guard-guide subassembly comprising a retractable bottom guard-guide that is retracted separate from retraction of the top, main guard-guide.
Figure 16:
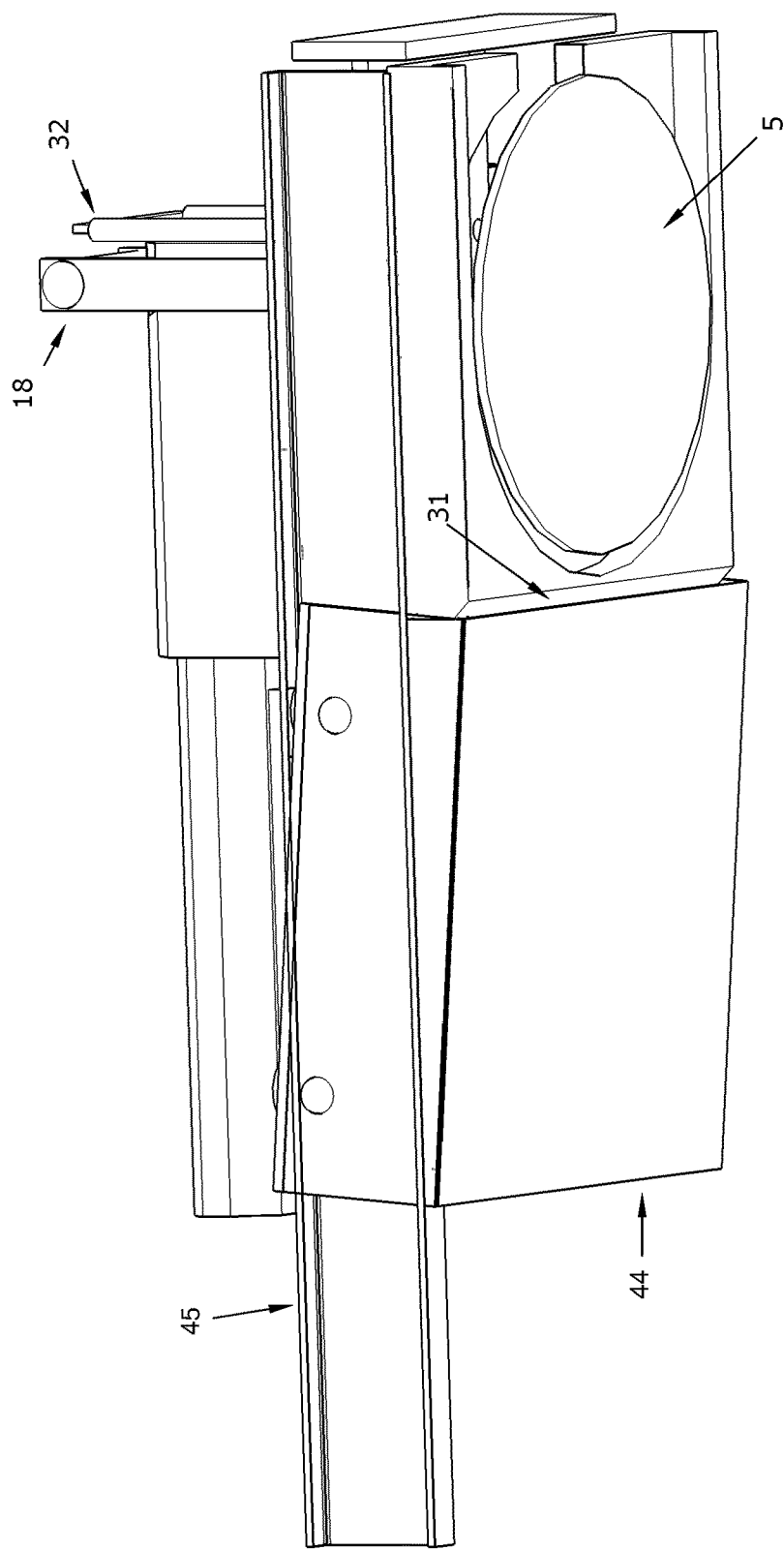
FIG. 16 depicts an oblique bottom view of one embodiment of a saw assembly comprising a guard-guide subassembly comprising a retractable bottom guard-guide that is retracted separate from retraction of the top, main guard-guide.

An exemplary embodiment of a saw assembly comprising a guard-guide subassembly comprising a retractable bottom guard-guide that is retracted separate from retraction of the top, main guard-guide is shown in FIGS. 13-17. For example, in one embodiment, the blade guard-guide subassembly 42 (FIG. 13) is utilized to produce a flush cut. As shown in FIG. 13, the saw may comprise a retractable (e.g., spring loaded) bottom guard-guide 44 with attached rollers 28, that ride on guide rails 45 and that can be retracted fully (e.g., to completely expose the bottom portion of the blade (e.g., for flush cutting)) separate from retraction of the top, main guard-guide 4. The top, main guard guide 4 will remain temporarily locked together with the electric motor subassembly, by top guard-guide lock 32 (FIG. 14 cutaway) comprised of horizontal trigger bar, springs 33, spring retainers 34 and vertical lock pins 35 that engage holes in top guard-guide 4 while a user's ring and little finger engage spindle 43, connected to bottom guard 44, and the user's hand slides rearward along the longitudinal axis of the handle of the electric motor subassembly 17 and paddle switch 16 so as to retract the bottom guard 44. Once the bottom guard 44 has moved (e.g., far enough aft) to allow its leading edge to engage the chamfer 31 (FIG. 13) on top guard-guide 4 and rollers 28 (FIG. 13) to engage guide rail cutouts 38, the bottom guard 44 tilts vertically so as to allow it to clear the bottom of the top guard-guide 4 (e.g., thereby permitting flush cutting). Once the bottom guard is fully retracted and the rollers 28 are fully engaged in cutouts 38, a portion of the tension of spring 29 is held by rollers 28 engaged in cutouts 38, another portion of the tension of spring 29 is relieved by the partial over-center effect of the tilt of bottom guard 44 as well as frictional forces of the leading edge of bottom guard 44 impinging on chamfer 31. Once the bottom guard 44 is fully retracted, the fingers of the user's other hand holding handle 18 may engage the horizontal bar of guard-guide lock 32, and lift it vertically so as to unlock the top guard-guide 4 from the electric motor subassembly 17 and allow the blade 5 to slide forward when the top guard-guide is pressed against work piece to be cut.

In some embodiments, a differential spring tension between bottom guard spring 29 (FIG. 13) and top guard-guide spring 14 is employed to allow the bottom guard 44 to retract and permit its rollers 28 (FIG. 13) to engage the guide rail cutouts 38 before blade 5 deploys. In some embodiments, an elliptically shaped cam subassembly is placed between spring 29 and bottom guard 44 (e.g., to further change leverage and/or add mechanical advantage so as to relieve tension of spring 29 (e.g., when bottom guard 44 is in the fully retracted position)).

In some embodiments, a crankset subassembly is placed between spring 29 and bottom guard 44 (e.g., in order to change leverage and/or add mechanical advantage so as to relieve tension of spring 29 (e.g., when bottom guard 44 is in the fully retracted position)).

In some embodiments, an operator must grip handle 18 with one hand, and motor subassembly handle 41 (FIG. 13) with the other, to complete a sensing electrical circuit (e.g., through grip switches (e.g., wired in series and/or amplified)) to operate a relay or bias a transistor, before the motor in the electric motor subassembly 17 will operate or for the motor to continue operating.

In some embodiments, the handle 18 and motor subassembly handle 41 (FIG. 13) are each charged with a small voltage the differential of which causes a milliampere current to travel through the operator's body when the operator grips handle 18 with one hand, and motor subassembly handle 41 (FIG. 13) with the other (e.g., the current can be detected by a sensor and amplified to operate a relay, or bias a transistor before the motor in the electric motor subassembly 17 will operate or for the motor to continue operating. In some embodiments, a small spring loaded mechanical safety lock (e.g., such as a springloaded pin, or a hook loaded by a tension spring, or other mechanical device) is installed on/in paddle switch 16 that must be physically depressed by the operator so as to allow paddle switch 16 to operate and complete a circuit to allow the motor in the electric motor subassembly 17 to operate or for the motor to continue operating. In some embodiments, the lock 32 is not installed, only differential spring tensions of springs 29 and 14 are utilized.

Figure 10:
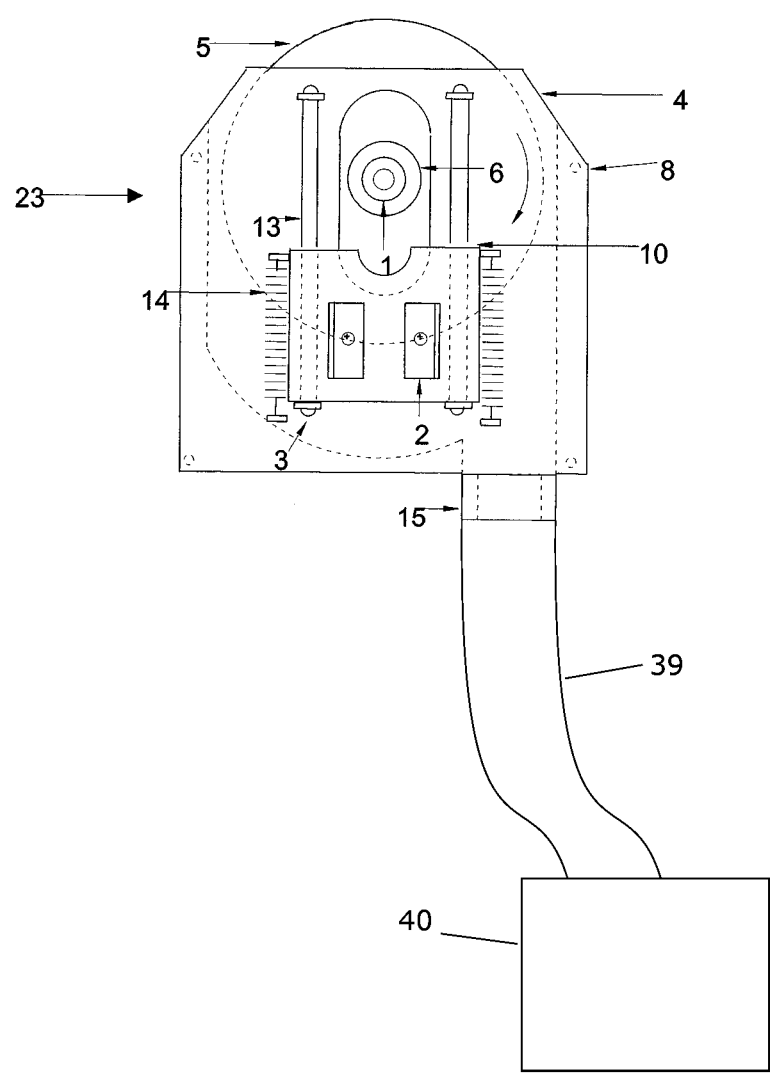
FIG. 10 shows one embodiment of a blade partially deployed beyond an angled guard-guide subassembly housing.
Figure 11:
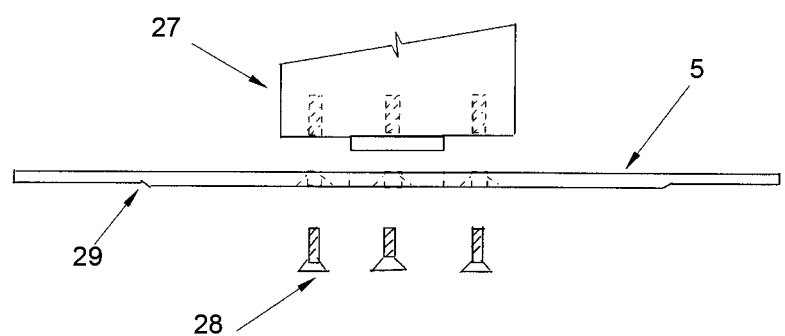
FIG. 11 depicts one embodiment of a blade ground or turned to produce a chamfered shoulder (e.g., for use with an integral spacer and bearing surface).

In some embodiments, a vacuum dust collector 40 is attached to a guard/guide exhaust port 15 by a flexible hose 39 (See FIG. 10). While any vacuum system of the art may be used, in some embodiments, the vacuum system comprises a high-efficiency particulate arrestance (HEPA) filter and/or system.

In some embodiments, the electric motor subassembly 17 possesses a trigger 16 (FIG. 1) with a momentary contact switch (e.g., a "dead man" switch), that when engaged/depressed, allows the motor to run, and when disengaged, results in no power to the motor. In some embodiments, the contact switch comprises a variable speed throttling switch. In some embodiments, the throttling switch permits the blade speed to ramp up or down (e.g., to gradually increase or decrease blade speed). In some embodiments, the maximum amount of retraction of the guard-guide subassembly 23 exposes 10% of the blade 5 (in some embodiments, the maximal amount of retraction exposes 10-25%, in some embodiments, the maximal amount of retraction exposes 25-50%, in some embodiments, the maximal amount of retraction exposes 50-75%, and in still other embodiments, the maximal amount of retraction exposes greater than 75%) of the blade 5. In some embodiments, the amount of retraction is dependent upon the position or setting of an adjustable stop (e.g., for adjustably controlling the depth at which the cutting blade (e.g., in vertical alignment with the cutting surface) can cut). In some embodiments, the saw assembly 19 comprises a handle 18 (FIG. 1). The handle 18 has many uses. For example, the handle 18 can be used to move the saw from place to place, to hold the saw steady when the saw is in use, or it can be used to push the saw assembly 19 against a surface 26, with the resulting pressure exerted by the surface 26 causing the guard-guide subassembly 23 to retract.

According to another aspect of the present invention, the blade 5 diameter (e.g., less than 5 inches) facilitates the cutting of material that a larger blade 5 (e.g., larger than 5 inches) may not cut well. For example, the saw assembly 19 of the present invention can be used to cut any type of surface, including, but not limited to, wood, plastic, metal, glass, cement, bone, ceramic or tile (e.g., the saw can be used to cut a window sash made of the aforementioned materials). In some embodiments, the saw assembly 19 can be used to undercut (e.g., a floor installer may use the saw assembly 19 of the present invention to undercut a baseboard, a door jamb, a base molding, or the like). In other embodiments, the saw assembly 19 can be used to cut window blind stops (e.g., during the removal and replacement of windows). In some embodiments, the saw assembly 19 of the present invention is used to cut a surface 26 under conditions in which it is not desired to have a blade exposed above the cutting surface 26 (e.g., for reasons such as safety, efficiency, cleanliness, etc.; See, e.g., FIG. 6). In some embodiments, the sliding bearing block 10 comprising return springs 14, and/or sliding lug 25, further comprises a regulator (acting as a depth gauge), that does not allow the guard-guide subassembly 23 to retract past a designated position. The use of a regulator is contemplated to allow a user to configure the saw assembly 19 to cut to a desired depth. Accordingly, in some embodiments, the regulator is demarcated with graduated length indicators (e.g., a ruler).

Figure 5A:
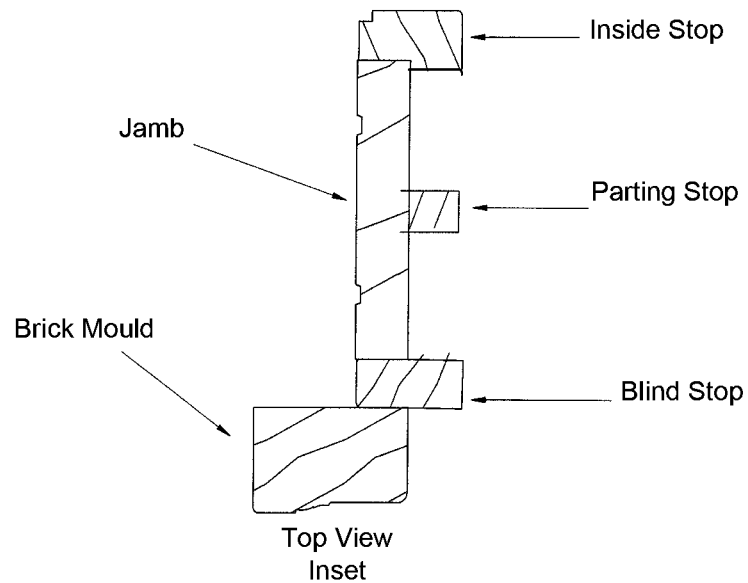
FIGS. 5A and 5B depict a window blind stop (A) before and (B) after cutting with a saw assembly constructed according to the invention.
Figure 5B:
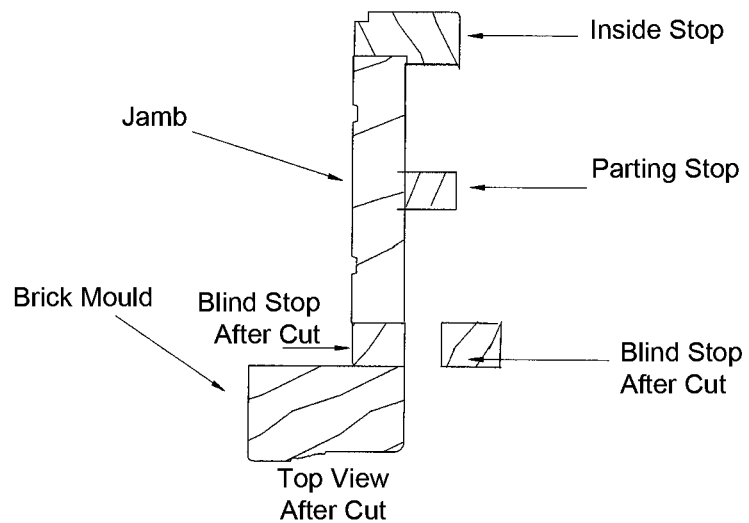

In some embodiments, the present invention provides a method of removing a window, comprising cutting stops present in the window, the cutting comprising using a saw configured so as not to have a blade exposed to the user during any portion of its use, wherein the method does not disrupt the inside window trim. In preferred embodiments, the user removes an existing sash of the window by cutting one or more stops (e.g., blind stops; See, e.g., FIGS. 5A-B) with a saw configured so as not to have a blade exposed to the user during any portion of its use (e.g., the saw assembly 19 of the present invention). Furthermore, the guard-guide sub-assembly 23 functions to guide the saw, allowing the saw to ride on the brick mould and enabling the saw to make a straight cut (See, e.g., FIGS. 5A-B). Thus, in preferred embodiments, the guard-guide permits a user to make a straight cut (e.g., either alone, or, using an existing, adjacent surface as a "rip fence" (e.g., for guiding the saw along a straight line)). In some embodiments, a companion piece may be used for guiding the saw (e.g., in medical uses, the companion piece may be a cutting guide (e.g., a speed block, all-in-one block, or four-in-one block)). In some embodiments, the window is replaced with a new window after the old window is replaced. In some embodiments, there is no need for new pieces of wood to assist in the replacement of the old window (e.g., in some embodiments, only caulk is needed). Using such a method dramatically decreases the amount of time needed to replace windows (e.g., double-hung windows) and decreases expenses (e.g., there is no need for new pieces of wood nor is any damage caused to the inside window trim) for work crews that are tasked with replacement of many windows (e.g., in an apartment complex, school, etc.). The time and cost savings are substantial.

Thus, the invention provides a saw assembly 19 that includes a guard-guide subassembly 23 configured to prevent exposure of the saw blade 5 to the user whether or not the saw is in use. A preferred embodiment utilizes a high speed 4-inch blade 5 mounted on a small, less than 10,000 rpm, right angle drive electric motor subassembly 17 of a commercially available 4-inch portable grinder. The resulting saw assembly 19 provides a device that is safe for cutting a variety of surfaces. The right angle drive makes it easy to manipulate, like a portable disk grinder. The smaller blade 5 does not damage surfaces that may be damaged when cut with a larger blade 5.

In a preferred embodiment, the saw assembly 19 of the present invention is configured to be fitted with blades 5 that are removable, reusable and/or disposable. Such blades 5 can be supplied by one or more suppliers. Suppliers of replaceable blades 5 may configure the blades for a particular purpose (e.g., for cutting blind stops during window replacement or for undercutting). In some embodiments, the replaceable blades 5 may be sold in kits designed for a particular purpose (e.g., a window replacement kit).

In some embodiments, the saw assembly 19 of the present invention may be generated by modifying an existing saw that lacks one or more elements of the present invention (e.g., a method of modifying an existing saw into the saw of the present invention by introducing to the existing saw a retractable, fully enclosing blade guard-guide subassembly).

The guard-guide subassembly of the present invention finds use with other types of saws. For example, the guard-guide subassembly can be modified to be compatible with a vibrating saw, a reciprocating saw or an oscillating saw. In some embodiments, the present invention provides a saw assembly comprising a motor; a linkage for converting rotating power of the motor into linear reciprocating movement; a slider shaft mounted at an end of the linkage having an angle of approximately 90 degrees with respect to the linkage; a slider, for attaching a saw blade, which moves reciprocatingly along the slider shaft, and a fully enclosing blade guard-guide subassembly, the blade guard-guide subassembly comprising a top main guard-guide slidably mounted on the electric motor subassembly and a bottom guard-guide plate fixed to the top main guard-guide assembly. In some embodiments, the blade used with a vibrating, oscillating or reciprocating saw is non-circular (e.g., is file shaped, See, e.g., blades described in U.S. Pat. No. 6,896,679, herein incorporated by reference in its entirety). In some embodiments, the blade guard-guide subassembly used with a vibrating, oscillating or reciprocating saw is spring-loaded. In some embodiments, the blade guard-guide subassembly fully encloses the non-circular blade (e.g., a file blade) until the blade guard-guide subassembly operably contacts a surface (e.g, a bone). In some embodiments, the operable contact comprises physical contact between a surface and the guard-guide subassembly such that the blade guard-guide moves into a retracted position, wherein the amount of retraction directly correlates with the amount of pressure asserted against the guard-guide subassembly by the surface. The present invention is not limited by the type of surface contacted.

Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. A saw assembly comprising:
an electric motor subassembly, the electric motor subassembly having a motor adapted to produce rotational movement about a first axis of rotation and a spindle rotatably powered by the electric motor for rotation about a second axis of rotation that is perpendicular to the first axis of rotation;
a blade mounted on the spindle; and
a blade guard-guide subassembly that encloses the blade, the blade guard-guide subassembly comprising a top main guard-guide and a bottom guard-guide plate, wherein the bottom guard-guide plate is configured to be slidably moveable between two positions, a first position wherein the bottom guard-guide plate fully encloses the blade together with the top main guard-guide and a second position wherein the bottom guard-guide plate is fully retracted independent of the top main guard-guide to expose the bottom portion of the blade;
wherein the top main guard-guide includes a rail having rail cutouts, and wherein the rail is coupled to a side of the top main guard-guide,
wherein the bottom guard-guide plate includes rollers guided on the rail;
wherein in the second position the rollers are partially received in the rail cutouts, a front end of the bottom guard-guide plate is biased against a rear end of the top main guard-guide, and a bottom surface of the bottom guard guide-plate is tilted above a surface to be worked on of a workpiece.

2. The saw assembly of claim 1, wherein the top main guard-guide is slidably mounted on the electric motor subassembly.

3. The saw assembly of claim 1, wherein the electric motor comprises a momentary contact switch.

4. The saw assembly of claim 1, wherein the electric motor comprise a variable speed throttling switch.

5. The saw assembly of claim 4, further comprising a mechanical lock that prevents the momentary contact switch from being depressed.

6. The saw assembly of claim 1, wherein the electric motor comprises a momentary contact switch comprising a variable speed throttling switch.

7. The saw assembly of claim 6, further comprising a mechanical lock that prevents the momentary contact switch comprising a variable speed throttling switch from being depressed.

8. The saw assembly of claim 1, wherein the blade contacts a cutting surface parallel to the bottom surface of the blade when the bottom guard-guide plate is fully retracted independent of the top main guard-guide.

9. The saw assembly of claim 1, wherein the bottom surface of the top main-guard guide protrudes beyond the bottom surface of the blade when the bottom guard-guide plate is in a fully retracted position.

10. The saw assembly of claim 1, wherein the blade guard-guide subassembly further comprises port for dust and/or debris.

11. The saw assembly of claim 10, wherein the port is attached to a vacuum.

12. A method of cutting a surface comprising contacting a surface with the saw of claim 1.

13. The method of claim 12, wherein the surface comprises wood, plastic, metal, cement, glass, ceramic, tile or bone.

* * * * *